(12) United States Patent
Masarie et al.

(10) Patent No.: US 7,657,521 B2
(45) Date of Patent: Feb. 2, 2010

(54) SYSTEM AND METHOD FOR PARSING MEDICAL DATA

(75) Inventors: Fred E. Masarie, Portland, OR (US); Stuart Lopez, Portland, OR (US); Michael I. Lieberman, Portland, OR (US)

(73) Assignee: General Electric Company, Schenectady, NY (US)

( * ) Notice: Subject to any disclaimer, the term of this patent is extended or adjusted under 35 U.S.C. 154(b) by 244 days.

(21) Appl. No.: 11/107,695

(22) Filed: Apr. 15, 2005

(65) Prior Publication Data

US 2006/0235881 A1 Oct. 19, 2006

(51) Int. Cl.
G06F 7/00 (2006.01)
G06F 17/27 (2006.01)
G06F 17/28 (2006.01)

(52) U.S. Cl. .................... 707/5; 704/2; 704/10
(58) Field of Classification Search ............ 707/1–3, 707/101, 104.1, 102; 704/9, 275, 231, 4, 704/2, 5, 10; 382/218; 705/2; 702/19
See application file for complete search history.

(56) References Cited

U.S. PATENT DOCUMENTS

| | | | | |
|---|---|---|---|---|
| 4,918,604 | A * | 4/1990 | Baum | 221/5 |
| 5,539,841 | A * | 7/1996 | Huttenlocher et al. | 382/218 |
| 5,664,109 | A * | 9/1997 | Johnson et al. | 705/2 |
| 5,832,450 | A | 11/1998 | Myers et al. | |
| 6,128,620 | A * | 10/2000 | Pissanos et al. | 707/102 |
| 6,137,911 | A * | 10/2000 | Zhilyaev | 382/225 |
| 6,182,029 | B1 * | 1/2001 | Friedman | 704/9 |
| 6,292,771 | B1 * | 9/2001 | Haug et al. | 704/9 |
| 6,415,295 | B1 * | 7/2002 | Feinberg | 707/104.1 |
| 6,542,902 | B2 * | 4/2003 | Dulong et al. | 707/104.1 |
| 6,556,964 | B2 * | 4/2003 | Haug et al. | 704/9 |
| 6,950,753 | B1 * | 9/2005 | Rzhetsky et al. | 702/19 |
| 7,478,033 | B2 * | 1/2009 | Wu et al. | 704/2 |
| 2002/0073138 | A1 * | 6/2002 | Gilbert et al. | 709/201 |
| 2002/0082868 | A1 * | 6/2002 | Pories et al. | 705/3 |
| 2002/0099534 | A1 * | 7/2002 | Hegarty | 704/2 |
| 2002/0128816 | A1 * | 9/2002 | Haug et al. | 704/4 |

(Continued)

OTHER PUBLICATIONS

Yi-Feng Lin et al. "A Maximum Entropy Approach to Biomedical Named Entity Recognition" BIOKDD 2004. 4th Workshop on Data Mining in Bioinformatics, Aug. 22, 2004 XP002401159.

*Primary Examiner*—Hung T Vy
(74) *Attorney, Agent, or Firm*—Hanley, Flight & Zimmerman, LLC (57) ABSTRACT

Certain embodiments of the present invention provide a system and method for processing medical data. The method includes the steps of identifying text strings in medical data, associating the text strings with standardized identifiers from a library, and outputting the standardized identifiers associated with the text strings. In an embodiment, a report and/or an order including the standardized identifiers associated with the text strings may be printed and/or stored. In an embodiment, the library may be modified to accommodate the text strings. A user and/or software program may be used to review the text strings to associate the standardized identifiers with the text strings, for example. In an embodiment, the text strings may be deconstructed into a plurality of sub-strings. A standardized identifier is then associated with each sub-string. The standardized identifiers may be numeric values, for example.

17 Claims, 3 Drawing Sheets

U.S. PATENT DOCUMENTS

| | | | |
|---|---|---|---|
| 2003/0105638 A1* | 6/2003 | Taira | 704/275 |
| 2003/0120458 A1* | 6/2003 | Rao et al. | 702/181 |
| 2003/0172081 A1* | 9/2003 | Dulong et al. | 707/100 |
| 2004/0019482 A1* | 1/2004 | Holub | 704/231 |
| 2004/0122787 A1* | 6/2004 | Avinash et al. | 706/50 |
| 2004/0148196 A1* | 7/2004 | Kalies | 705/2 |
| 2005/0234740 A1* | 10/2005 | Krishnan et al. | 705/2 |
| 2005/0251384 A1* | 11/2005 | Yang | 704/10 |

* cited by examiner

210 — Identify an observation to be scrubbed.

220 — Analyze data from an observation table.

230 — Configure control tables based on the information.

240 — Write the original string and scrubbed string to test table for further analysis.

250 — Refine control information if necessary and rerun test.

260 — Once control information is sufficiently defined, data is loaded to an observation fact table.

SYSTEM AND METHOD FOR PARSING MEDICAL DATA

RELATED APPLICATIONS

Not Applicable

FEDERALLY SPONSORED RESEARCH OR DEVELOPMENT

Not Applicable

MICROFICHE/COPYRIGHT REFERENCE

Not Applicable

BACKGROUND OF THE INVENTION

The present invention generally relates to parsing medical data. In particular, the present invention relates to a system and method for parsing medication instructions.

Hospitals typically utilize computer systems to manage the various departments within a hospital and data about each patient is collected by a variety of computer systems. For example, a patient may be admitted to the hospital for a Transthoracic Echo (TTE). Information about the patient (e.g., demographics and insurance) could be obtained by the hospital information system (HIS) and stored on a patient record. This information could then be passed to the cardiology department system (commonly known as the cardio vascular information system, or CVIS). Typically the CVIS is a product of one company, while the HIS is the product of another company. As a result, the database between the two may be different. Further, information systems may capture/retain and send different levels of granularity in the data. Once the patient information has been received by the CVIS, the patient may be scheduled for a TTE in the echo lab. Next, the TTE is performed by the sonographer. Images and measurements are taken and sent to the CVIS server. The reading physician (e.g., an echocardiographer) sits down at a review station and pulls the patient's TTE study. The echocardiographer then begins to review the images and measurements and creates a complete medical report on the study. When the echocardiographer completes the medical report, the report is sent to the CVIS server where it is stored and associated with the patient through patient identification data. This completed medical report is an example of the kind of report that could be sent to a data repository for public data mining. Medication instructions, such as documentation and/or prescription, may also be generated electronically and saved in a data repository.

Today, medical device manufacturers and drug companies face an ever-growing challenge in collecting clinical data on the real-life utilization of their products. As patient medical reports are becoming computerized, the ability to obtain real-life utilization data becomes easier. Further, the data is easier to combine and analyze (e.g., mine) for greater amounts of useful information.

As medical technology becomes more sophisticated, clinical analysis may also become more sophisticated. Increasing amounts of data are generated and archived electronically. With the advent of clinical information systems, a patient's history may be available at a touch of a button. While accessibility of information is advantageous, time is a scarce commodity in a clinical setting. To realize a full benefit of medical technological growth, it would be highly desirable for clinical information to be organized and standardized.

Even if clinical or image-related information is organized, current systems often organize data in a format determined by developers that is unusable by one or more medical practitioners in the field. Additionally, information may be stored in a format that does not lend itself to data retrieval and usage in other contexts. Thus, a need exists to structure data and instructions in a way that is easier to comprehend and utilize.

Prescriptions written by a physician include information such as medication, formulation (e.g., liquid, tablet, capsule), dosage (e.g., how many formulations), route (e.g., oral), duration, frequency/interval, and/or qualifiers (e.g., as needed or as directed). An electronic medical record system, such as Logician®, may standardize and/or process information such as medication, form, and quantity (e.g., Ibuprofen 100 mg tablets), but the remainder of the prescription is typically free form (e.g., a free form text string). If some information is known, other prescription information may be determined (e.g., a number of pills and how many pills to take per day provides duration). Thus, a system for processing free form prescription information would be highly desirable.

Medical technicians and clinical systems work with physicians ordering prescriptions and documenting medications in electronic medical records, for example. Third party knowledge bases have complete lists of medications that patients may purchase, including dosage, form, and route. However, it is not enough to only know dosage, form, and route information. It is important to know how often the medication should be taken and how much of the medication should be taken. This and other information may be found in significant instructions or "sigs" entered by a prescribing physician.

Sigs are not currently standardized and vary from physician to physician. However, information such as dosage, form, and route is typically standardized. Thus, a clean, clear and complete instruction for administration of a medicine would be highly desirable. Additionally, a reliable system for reading and interpreting sigs would be highly desirable. Improved reliability in sig interpretation is important for patient safety. Reliable reading and storing of sigs would also improve quality of patient care. Reduced error in sig translation also saves money for healthcare providers, pharmacies, and insurers. Structured data capture of a sig interpretation may facilitate data mining and decision support, for example.

In an electronic medical record or report, clear information is desirable, but many physicians will not use a system that requires them to be too neat and structured in inputting data and instructions. Many physicians prefer free form instruction drafting. Thus, a system that balances between natural and structured language would be highly desirable. Additionally, it would be desirable to accommodate abbreviations and medical jargon (e.g., "1 po qd"="one tablet by mouth once a day"), as well as multiple variants of commonly used instructions. Thus, a system for efficient and effective translation of varied commands, notes, and instructions into finite, discrete, quantitative information would be highly desirable.

Therefore, there is a need for a system and method for processing medication instructions.

BRIEF SUMMARY OF THE INVENTION

Certain embodiments of the present invention provide a system and method for processing medical data. Certain embodiments provide an improved method for processing significant instructions in medication orders, for example. The method includes the steps of accessing medical data, extracting at least one text string containing significant instructions from the medical data, and parsing the text string(s) to associate at least one identifier with each of the text string(s). The method may also include deconstructing the text string(s) into a plurality of sub-strings for each of the text string(s). In an embodiment, the parsing step includes associating at least one identifier with each sub-string. Additionally, a user and/or software program, for example, may review the text string(s) to associate the identifier(s) with each of the text string(s). In an embodiment, the identifiers are numeric values, for example.

Certain embodiments provide an improved method for processing medical data. The method includes the steps of identifying text strings in medical data, associating the text strings with standardized identifiers from a library, and outputting the standardized identifiers associated with the text strings. In an embodiment, a report and/or an order including the standardized identifiers associated with the text strings may be printed and/or stored. In an embodiment, the library may be modified to accommodate the text strings. For example, if a text string has not been seen before, the library may be modified and/or replaced to associate an identifier with the text string. A user and/or software program may be used to review the text strings to associate the standardized identifiers with the text strings, for example. In an embodiment, the text strings may be deconstructed into a plurality of sub-strings. A standardized identifier is then associated with each sub-string. The standardized identifiers may be numeric values, for example. In an embodiment, the text strings include significant medication instructions or "sigs."

Certain embodiments provide a system for processing medication instructions. The system includes a data source including medical data and a data processor receiving data from the data source and processes the data according to a lexicon. The data processor deconstructs the data into segments and parses the segments. The medical data may include medication instructions and/or observation values, for example. In an embodiment, the data processor deconstructs the data into significant instructions and parses the significant instructions. The data processor may associate a numerical identifier with each of the segments, for example.

Certain embodiments include a computer-readable storage medium including a set of instructions for a computer. The set of instructions include an extraction routine extracting at least one alphanumeric string containing significant instructions from a medical instruction. The set of instructions also include a parsing routine parsing the at least one alphanumeric string to associate at least one identifier with each of the at least one alphanumeric string.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments of the present invention process significant instructions or "sigs" in medication orders, for example. For purposes of illustration only, a few examples of sigs may include "1 tab po qd" ("one tablet by mouth once a day"), "10 units sc qAm and 5 units sc qHS" ("10 units injected subcutaneously every morning and 5 units injected subcutaneously at bedtime"), "two pills 2 am and 2 pm (total 80 mg/da)" ("two pills at 2:00 AM and at 2:00 PM (total dosage 80 mg per day)"), "0.5-1 mg every 4 to 6 hr prn" ("0.5 to 1 mg every 4 to 6 hours as needed"), and/or "1 daily except 1.5 tabs m-w-f" ("1 tablet daily except 1 and ½ tablets on Mondays, Wednesdays, and Fridays"). Medication orders and other text or data strings may be parsed to place sigs and other information contained in the text into a standardized or numeric format. The format allows instructions or other data to be transmitted, stored, manipulated, and/or otherwise processed between multiple sources and/or users, for example.

Figure 1:
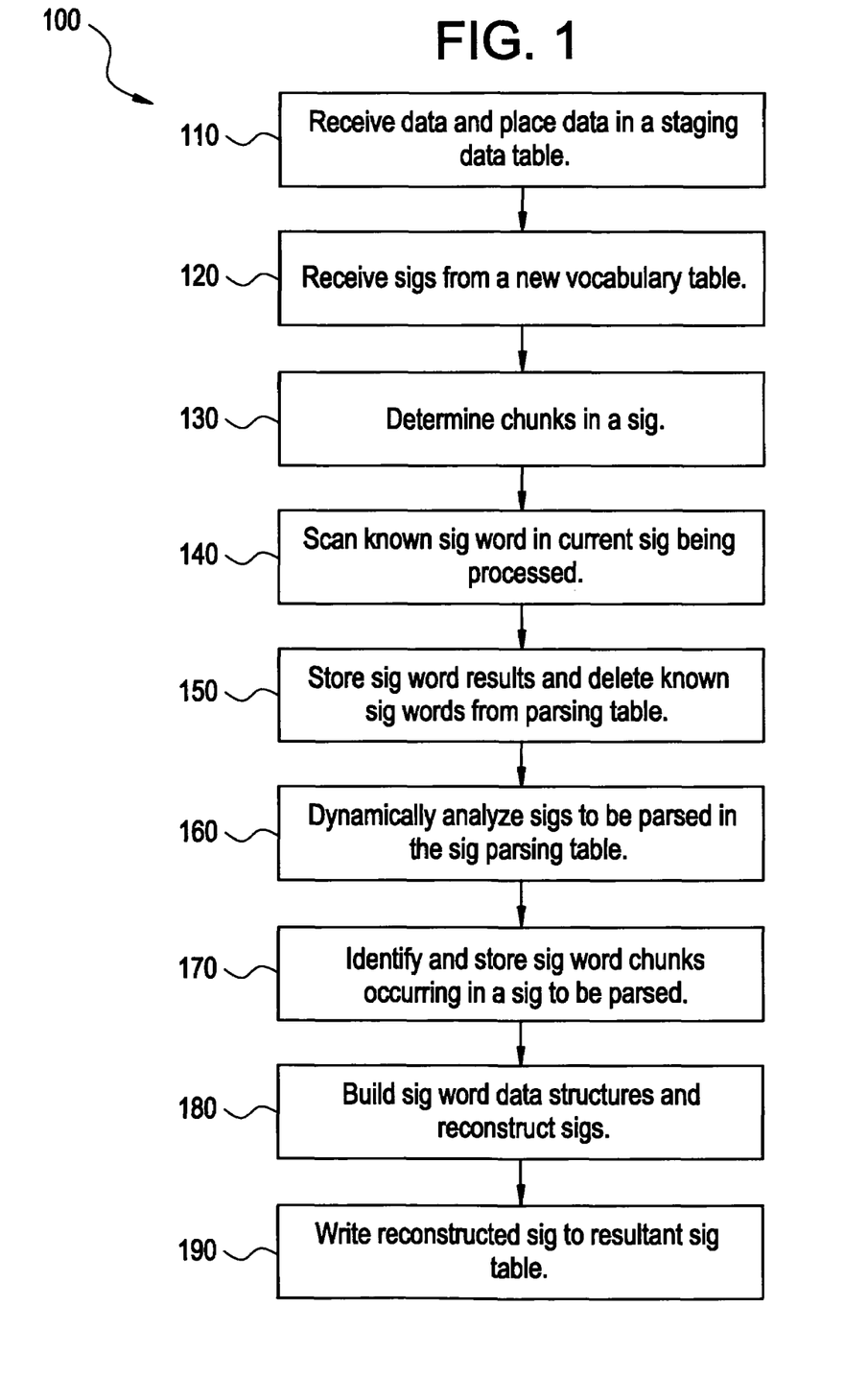
FIG. 1 illustrates a flow diagram for a method for processing significant instructions in accordance with an embodiment of the present invention.

In an embodiment, sigs may be obtained from electronic medical records (EMRs), optical character recognition (OCR), a medication order system, a database, a computerized physician order entry (CPOE), and/or other electronic format, for example. In an embodiment, an automated mechanism extracts sigs received from an electronic medical record system, such as Logician®, or other data source and sends strings representing the sigs to a vocabulary processing server, such as a Terminology server. In an embodiment, the data sent includes a usage count. The usage count may be used to determine which sigs to process, for example. The usage count may also be used to determine parsing priority among a plurality of sigs. In an embodiment, only the strings received since the last transfer to the vocabulary processing server are sent with the usage count for the period between the last transmission and the current transmission. FIG. 1 illustrates a flow diagram for a method 100 for processing significant instructions in accordance with an embodiment of the present invention.

First, at step 110, data is initially received at the Terminology or other vocabulary server and placed in a staging data table. An automated process determines whether each newly staged table entry has been seen before (e.g., whether the data in the table already resides in a processed vocabulary table or other data structure). If the table entry has been examined before, historical usage counts are incremented by the newly received counts. If the table entry (or entries) has not been processed before, then the newly received sig is written to the new vocabulary table (e.g., "SIG") and usage counts are updated. In an embodiment, the sig is assigned a sig identifier (a "sig_id") that may be used in subsequent processing. An insert trigger exists in the new vocabulary table that stores the sig_id for all new sigs in a sig parsing table (e.g., "SIG TO PARSE"). The sig parsing table may serve as an automated parsing driving mechanism. In an embodiment, "SIG TO PARSE" includes a sig, a corresponding code for the sig, and a usage count. In an embodiment, the "SIG TO PARSE" table includes a sig_id or code, and the sig and usage count are available by reference from other table(s).

Next, at step 120, using the "SIG TO PARSE" table as a driver, sigs which have not yet been parsed are retrieved from the new vocabulary table. An initial step in parsing is to attempt to identify any new words and/or phrases of significance, such as dose/route phrases, that appear in the sig being parsed. A dose/route phrase consists of a number followed by a dose/route "tag". The tag may include embedded whitespace and/or followed by additional whitespace-number-dose/route tag combinations, for example. Words or phrases may be of varying types including dose/route, route, interval, duration, standard, indication, and/or stop word, for example. For example, a sig "1 tab po qd" includes words "1 tab po" and "qd". The new dose/route phrases are written to a sig word table (e.g., "SIG WORD OR PHRASE") for subsequent interpretation by a Terminology Specialist or other system.

In an embodiment, phrases are identified as follows. A dose/route phrase is identified by looking for the first numeric/valid-sig-uom (unit of measure) combination. The valid-sig-uom tags, such as "tab", "mg/d", and "p.o." may be stored in a table (e.g., "SIG UOM"). In an embodiment, a character following the uom tag in the string is followed by a whitespace or other delimiter. Certain embodiments attempt to handle occurrence of non-unit/uom numerics eventually followed by actual unit/uom numerics. In an embodiment, the initial dose/route phrase is assigned a word count of two, for example.

At step 130, once the first dose/route phrase is identified, any additional whitespace dose/route phrases following the first phrase are determined. For example, succeeding dose/route phrases may be concatenated to the initial phrase, and the word count may be incremented by two, for example, for each. Once non-whitespace dose/route characters are encountered following the dose/route phrase being built, a dose/route parse is complete. If a resultant dose/route phrase does not exist in the sigword table ("SIG WORD OR PHRASE"), then the extracted phrase is stored to "SIG WORD OR PHRASE" with a word type of "dose/route", for example.

Then, at step 140, once "SIG WORD OR PHRASE" has been potentially augmented with the new dose/route phrase found in the current sig, a scan is performed to determine which "chunks" (words and/or phrases), of the chunks (dose/route and otherwise) contained in "SIG WORD OR PHRASE", occur in the current sig being parsed. For example, "1 tab po qd" contains two chunks: "1 tab po", which is a dose/route word, and "qd", which is an interval word. The determination may be repeated for other phrases, for example, that include both predefined tags representative of the type of phrase and numeric data associated with the tag, such as interval, duration, and frequency. In an embodiment, this search is performed in descending order starting from the longest chunks. As each chunk is identified as being embedded in the sig, the chunk is written to a sig parse working table (e.g., "SIG PARSE") provided the chunk does not overlap any chunk already identified as being embedded in the sig and already written to the working table.

By processing the longest chunks first and identifying overlays when a shorter chunk overlaps a longer chunk, processing may focus on the longest, and presumably most valuable, chunks. In an embodiment, only those chunks which do not overlay a longer chunk are written to the sig parse working table. At step 150, once the scan identifying which chunks occur in the sig is completed and the results are stored in the working table, the associated row for the current sig is deleted from "SIG TO PARSE". At step 160, once the working table is populated with the information for all sigs to be parsed, the table is dynamically analyzed for performance.

Next, at step 170, chunks occurring in a sig are identified and stored in a permanent table to remember which words or phrases occur in a sig (.e.g., "SIG SIGWORD"). The working table, "SIG PARSE", is a driver for this process. For each sig associated with at least one row in the working table, a sig_id/sigword_id combination is stored in "SIG SIGWORD". The chunk substring is stripped from an image of the associated sig string in order that, once all identified chunks are captured to "SIG SIGWORD", a determination of whether any residue of the original sig remains. A residue is any character(s) other than whitespace and special characters. If any residue remains, the residue string is stored in a residue data structure for later evaluation and potential manual chunk addition to the "SIG WORD OR PHRASE". Once the "SIG SIGWORD" record has been built for a given sig, the associated row is deleted from the working table.

At step 180, once "SIG SIGWORD" records are built for sigs of interest, the sigs must be "reconstructed" to determine an overall meaning of the sig. That is, the "bucket" data or value-added attributes associated with a sig is determined based upon which chunks were identified as being embedded in the sig and combining the value-added attributes associated with these individual words or phrases. During the sig reconstruction phase, business logic or reconstruction rules may be applied to help ensure that a value-added data contributed by each constituent word or phrase does not conflict with a value-added data contributed by other constituent words or phrases. The "SIG SIGWORD" table may be the driver for the reconstruction process.

In an embodiment, rules for reconstruction may include the following, for example. First, reconstruction occurs for sigs not already represented in a resultant sig table (e.g., "RECONSTRUCTED SIG"). Reconstruction occurs for sigs with constituent sig words marked as having been analyzed and approved by a Terminology Specialist or other verification system (e.g., status=1003). Reconstruction is performed based on 1) dose/route, 2) route, 3) interval, 4) duration, 5) other prescription information as identified by word type in a sig word data structure, for example.

In certain embodiments, software and/or reporting flags may be set based on sig or other data. If a low/high dose, low/high interval, or low/high duration value, for example, has already been identified during the reconstruction process and a subsequent sig word is associated with conflicting low/high dose, interval or duration and/or a conflicting low/high dose unit value, for example, then a "complex_sig" flag may be set and no other bucket values are retained for the sig. The complex_sig value may then be separately processed by a technician and/or system, for example. In an embodiment, if route information is supplied via a sig word of type "route" and no low dose information is associated with the sig (indicating no "dose/route" information), then a low dose value is set to 1 and a low dose unit is set to "EA", for example.

In an embodiment, if a sig word associated with the sig includes a "prn_flag", the flag implies an instruction of "as needed". If prn_flag="Y", then the resultant prn_flag for the sig="Y". If any sig word associated with the sig includes an "as_directed_flag"="Y", then the resultant as_directed_flag for the sig="Y".

If a low interval has been identified, but no low dose nor low dose unit values have been set, no sigword associated with the sig is of type "dose/route" and no residue remains after parsing, then low_dose is set to 1 and low_dose_unit is set to "EA", for example. If a high interval has been identified, but no high dose nor high dose unit values have been set, no sigword associated with the sig is of type "dose/route" and no residue remains after parsing, then high_dose is set to 1 and high_dose_unit is set to "EA", for example.

Other flags may include a time of day flag, such as "am_flag", "midday_flag", or pm_flag", a parse complete flag indicating that a sig has been parsed, a reparse flag, indicating that all or part of a sig is to be reparsed, and/or a status flag indicating sig parsing status, for example. A sig residue string may also be generating including data not processed during sig parsing.

Then, at step 190, the resultant reconstructed row is written to a resultant sig table (e.g., "RECONSTRUCTED SIG"). In an embodiment, if the complex_sig flag is set, the complex_sig_flag value is set in the row being written, and further processing may be performed with respect to the sig. In an embodiment, a reconstructed sig may be written to a database, such as a reporting database, and used to generate one or more reports, such as a medication instruction report, diagnosis/treatment report, and/or clinical trial report. For example, one could generate reports on daily doses for medications, and/or how frequently a medication is supposed to be taken.

Thus, certain embodiments provide a system for sig parsing in a prescription, report or other document, for example. An entire sig may be written to a table to be examined by a terminology specialist or terminology software. Alternatively, a sig may be divided into words and/or phrases (chunks). Previously parsed words and/or phrases may be identified. Significant words and/or phrases which have not been previously parsed may be written into a table for identification by a technician and/or software program. Values, such as code values, may then be assigned to chunks by the technician and/or software. Removing previously parsed chunks from the table of unknown sig chunks reduces an amount that a person and/or software program evaluates.

For example, the system locates text that indicates dosage and route for a medication. The system examines the text to determine if all or part of the text has previously been evaluated and assigned a code. If at least a portion of the text has not been previously evaluated, then the system processes the text to associate a numeric with dosage and route information, as well as interval information and other information. That is, sigs are divided into chunks. A person and/or system determines a meaning of the chunks. Then, the system reconstructs the overall sig, applying business logic in the process to ascertain an overall meaning of the instruction.

Thus, in certain embodiments, the sig processing system is an adaptive system. That is, the more information the system sees, the less information the system processes. Additionally, the system may utilize synonyms for chunks in order to provide a more flexible, faster processing system.

In an embodiment, a database, such as an offline database, is created separate from an electronic medical record. The database may be used for research and quality reporting, for example. Sig processing may be performed in real time or substantially real time and/or may be performed at a later time, for example. Processed sigs may be stored in electronic medical records, for example. The electronic medical records may then be sent to pharmacies for prescription. Processed sigs may be used to complete missing information and/or determine prescription refill information, for example.

In an embodiment, doctors may be provided with a menu of commands to simplify and standardize sigs. By using standard, commonly referenced commands, the system may only have to process commands not found in a standard list or lexicon, for example.

In certain embodiments, information may be used to assess prescribing patterns for safety purposes. Tools may be built to provide physicians and pharmaceutical companies with an understanding of how well guidelines are being followed. Statistics may be generated regarding quality of care and/or safety, for example. Additionally, certain embodiments may be used to provide pharmacological outcomes research. By referencing a database of patient information, effectiveness of treatment may be evaluated. Parsed data may be used to evaluate safety concerns and reduce side effects due to certain dosages and drugs, for example.

Such an analysis may also be applied prospectively to organize and analyze clinical trial data. In an embodiment, physicians select from a pre-determined list of instructions when prescribing a medication in a clinical trial. Thus, tighter controls and reduced variation may be introduced in the trial.

In an embodiment, data from prescriptions and other clinical trial data may be collected and used to expedite clinical trials. Data from multiple customers/patients may be extracted and aggregated. Protected information may be removed (i.e., de-identification or anonymization of patients). A patient population may be defined for analysis. A database including patient trial data may then be queried. Data with anonymous identification tags may be extracted and re-associated with some or all identification information for clinical trials. Data may be aggregated from multiple sources, anonymized, and sold to pharmaceutical companies. Clinical trial recruitment, data processing, and analysis may be centralized in one system and/or location. Laboratory data, images, notes, and other information may be integrated and processed. History, demographics, genetic information, and other information may be tracked and integrated into electronic medical records, for example. Thus, a clinical trial process may be streamlined.

In an embodiment, observation values in medical reports or other documents may also be processed. For example, a medical report table, such as a Logician® medical data table, may include one or more observation values from an examining physician or other medical professional. The observation value (e.g., "obs" or "obsvalue") field may be a free-format field, for example. In certain schema, a free-format obsvalue field from table data is converted to a numeric value when the obsvalue data is loaded into the observation fact table in a Star schema, for example. Observation terms may be "scrubbed" or parsed and loaded into a reporting database to associate a numeric value with observation data.

Figure 2:
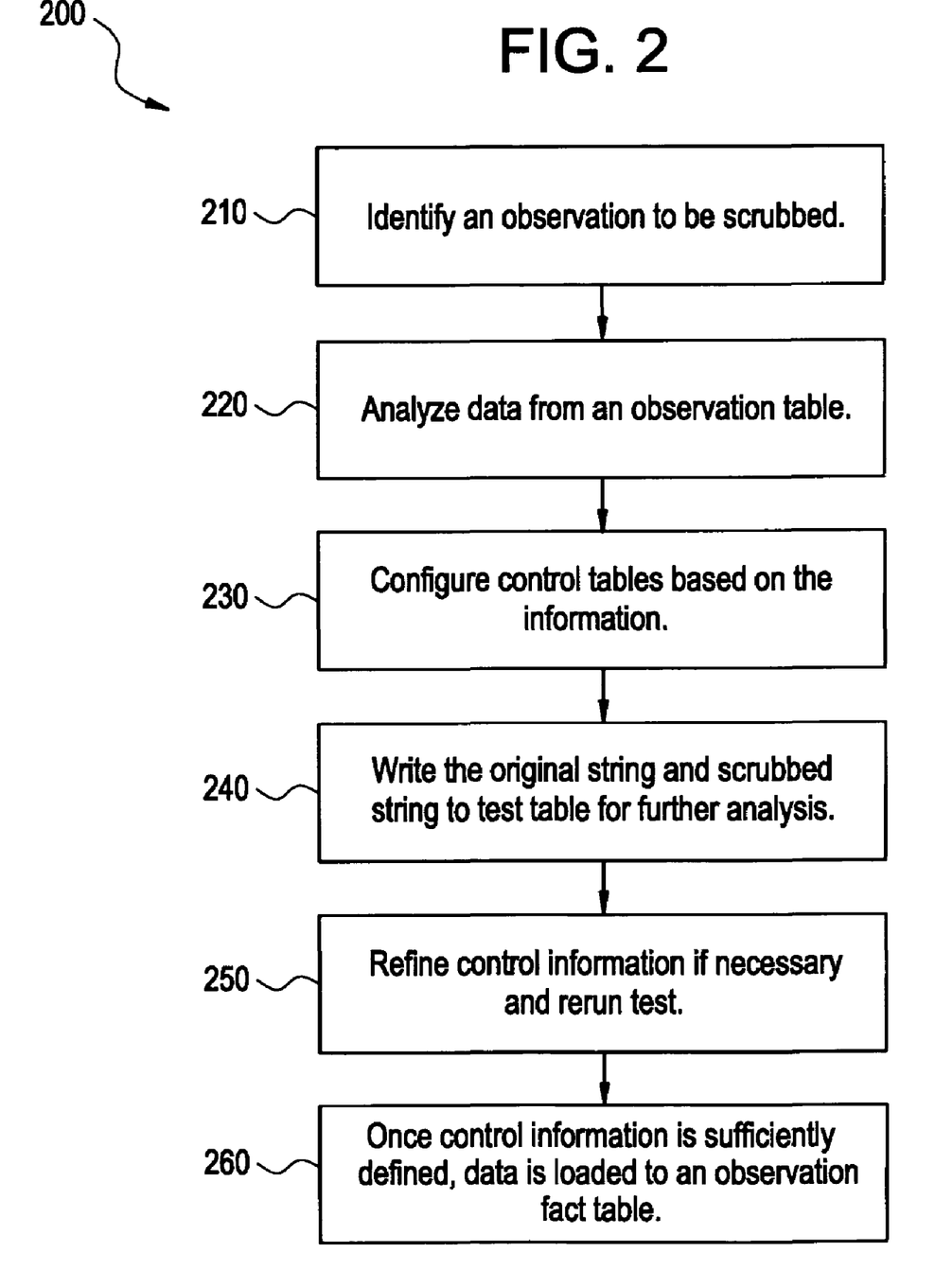
FIG. 2 shows a flow diagram for a method for observation value scrubbing in accordance with an embodiment of the present invention.

FIG. 2 shows a flow diagram for a method 200 for observation value scrubbing in accordance with an embodiment of the present invention. In an embodiment, the method 300 involves the following steps. First, at step 210, an observation to be scrubbed is identified. Identification may be initiated by a customer request or automatically identified, for example. Then, at step 220, data from an observation hold table is analyzed at a high level by someone with a clinical background, and a standard unit of measure, alternate units of measure, and an acceptable range are determined, for example. Alternatively, a software program may be used to analyze the data from the observation hold table. Next, at step 230, control tables are configured based on the information provided.

Then, at step 240, a test run writes the original string and the scrubbed string to a test table for further analysis, and a "clean scrub" percentage is determined. Observation values may fall into four buckets, for example. For example, a result of "−1" indicates that the system was unable to scrub the field, and the value contains no numeric information. A result of "−2", for example, indicates that the system was unable to scrub the field, and a numeric value was found with unrecognized units of measure. A result of "−3" indicates that the field was scrubbed, but the numeric value derived is outside of acceptable range, for example. A result of "value", for example, indicates that the field was scrubbed to a numeric value, expressed in terms of a standard unit of measure defined for the observation.

Next, at step 250, control information (ranges, additional units of measure, etc.) is refined if necessary, and the test is rerun. At step 260, once control information is sufficiently defined, data is loaded to an observation fact table.

Figure 3:
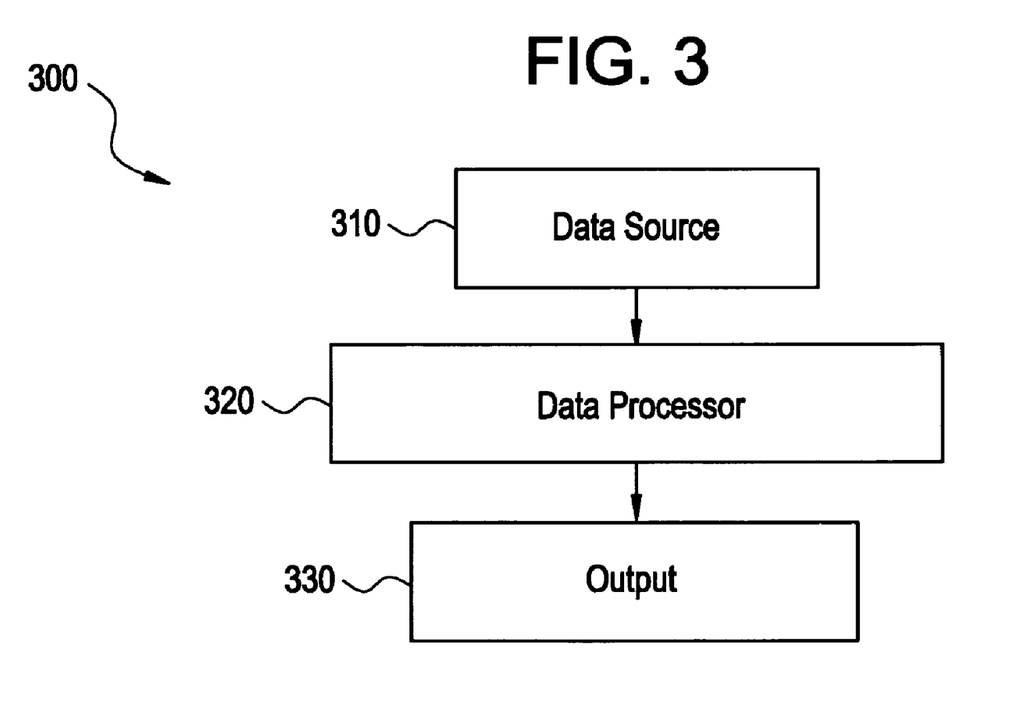
FIG. 3 illustrates a data processing system for processing medical data and instructions used in accordance with an embodiment of the present invention.

FIG. 3 illustrates a data processing system 300 for processing medical data and instructions used in accordance with an embodiment of the present invention. The system 300 includes a data source 310, a data processor 320, and an output 330. The data source 310, data processor 320, and output 330 may communicate via wired or wireless connections that interconnect one or more of the data source 310, data processor 320, and output 330. The data source 310, data processor 320, and/or output 330 may be embodied in separate units and/or combined in various combinations. For example, a computer may house the data source 310, data processor 320, and output 330.

The data source 310 includes data, such as a medical record (electronic or paper with OCR), text file, or other medical data. The data processor 320 is a software and/or hardware processing unit that receives data from the data source 310. The data processor 320 analyzes the data and may deconstruct the data into segments or "chunks". The data processor 320 then parses, scrubs, or otherwise processes the data in whole or in part according to a lexicon and/or set of rules or standards, for example. The data processor 320 may process the data according to instructions from a software program and/or from a user. For example, a technician may configure the data processor 320 to parse sigs in the data. Alternatively or in addition, the technician may configure the data processor 320 to parse observation values in the data. In an embodiment, the data processor 320 includes a library of identifiers or values to be associated with parsed data. The library may be updated or replaced by a user and/or software update, for example.

After the data processor 320 has processed the data from the data source 310, the data processor 320 transmits the processed data to the output 330. The output 330 may include a printer, a memory, and/or other transmission or storage device, for example. The output 330 may store the processed data (e.g., in an electronic medical records database) and/or may generate a printed output (e.g., a prescription), for example.

Thus, certain embodiments provide a system and method for parsing data in a clinical information system. Certain embodiments convert data into a format usable by the clinical information system for reporting, processing, and clinical diagnosis/treatment, for example. A vocabulary may be used to convert text strings into concepts. Data may be cleansed of protected health information. Words may be mapped to a semantically consistent concept. Junk data may be removed using the concept rather than raw data, for example.

Certain embodiments translate sigs into meaningful numbers or facts. A string is parsed and decomposed into parts. Parts of the string that have a numerical significance are identified. The string is then recomposed to summarize the sig. Thus, medication or prescription instructions may be interpreted.

Certain embodiments translate from natural language to clinical concept with no protected information. Certain embodiments provide an automated system for translation. For example, the system may evaluate a patient's chief complaint and match then complaint to a medical concept for easier processing and interpretation.

Certain embodiments scrub medical data to convert free-format observation value fields into numeric values. Certain embodiments, define an observation term vocabulary for scrubbing observation value language into observation terms for reporting. Certain embodiments compare an original string and a scrubbed string to ensure that information is sufficiently defined before loading data into an observation fact table. Thus, free-form text strings may be mapped to a specific value or set of specific values. Free-form text values are processed to extract more defined information from the free-form strings.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for processing significant instructions in medication orders, said method comprising:

accessing medical data including at least one medication order;

extracting at least one alphanumeric text string containing significant instructions from the at least one medication order, wherein said at least one alphanumeric text string containing significant instructions comprises at least one free form alphanumeric text string;

identifying one or more significant instructions in each of the at least one alphanumeric text string;

parsing each of the one or more identified significant instructions to identify one or more words or phrases in each significant instruction;

classifying known words or phrases in the one or more identified words or phrases according to a vocabulary table by assigning an identifier from the vocabulary table to each known word or phrase in the one or more identified words or phrases;

analyzing unknown words or phrases in the one or more identified words and phrases to assign an identifier to each of the unknown words or phrases in the one or more identified words or phrases and adding the identifier to the vocabulary table for use in significant instruction parsing, wherein the identifier is associated with an incrementing usage count to determine significant instruction priority for processing;

reconstructing each of the one or more significant instructions as codified significant instructions using the identifiers associated with the known and unknown words or phrases in each of the identified significant instructions; and storing the one or more codified significant instructions in a medication order.

2. The method of claim 1, further comprising deconstructing the at least one alphanumeric text string into a plurality of sub-strings for each of the at least one alphanumeric text string.

3. The method of claim 2, further comprising associating an identifier with each sub-string.

4. The method of claim 1, wherein the at least one identifier comprises a numeric value.

5. The method of claim 1, wherein at least one of a user and a software program review each of the unknown words or phrases in the one or more identified words or phrases to associate an identifier with each of the unknown words or phrases.

6. The method of claim 1, further comprising adding each of the unknown words or phrases and one or more assigned identifiers to the vocabulary table after each of the unknown words or phrases has been analyzed.

7. A computer-implemented method for processing medical data, said method comprising:
   identifying alphanumeric text strings in medical data, wherein said alphanumeric text strings comprise one or more significant instructions including one or more free form alphanumeric text strings;
   parsing the alphanumeric text strings to identify previously identified portions and unknown portions;
   analyzing unknown portions of the alphanumeric text strings;
   associating the previously identified portions and unknown portions of the alphanumeric text strings with standardized identifiers from a library, wherein standardized identifiers for previously identified portions of the alphanumeric text strings are found in a vocabulary table and standardized identifiers for unknown portions of the alphanumeric text strings are generated and added to the vocabulary table, wherein each standardized identifier is associated with an incrementing usage count to determine significant instruction priority for processing; and
   outputting the standardized identifiers associated with the alphanumeric text strings to form instructions in a medication order.

8. The method of claim 7, wherein the outputting step comprises printing at least one of a report and an order including the standardized identifiers associated with the alphanumeric text strings.

9. The method of claim 7, wherein the outputting step comprises storing at least one of a report and an order including the standardized identifiers associated with the alphanumeric text strings.

10. The method of claim 7, further comprising modifying the library to accommodate the alphanumeric text strings.

11. The method of claim 7, wherein at least one of a user and a software program review the alphanumeric text strings to associate standardized identifiers with the alphanumeric text strings.

12. The method of claim 7, further comprising deconstructing the alphanumeric text strings into a plurality of substrings.

13. The method of claim 12, wherein the associating step further comprises associating a standardized identifier with each sub-string.

14. The method of claim 7, wherein the standardized identifiers comprise numeric values.

15. A system for processing medication instructions, said system comprising:
   a data source including medical data, the medical data including at least one medication instruction, wherein said medication instruction comprises one or more significant instructions including at least one free form alphanumeric text string; and
   a data processor receiving said medication instruction from the data source and processing said medication instruction according to a lexicon, wherein the data processor deconstructs said medication instruction into segments and parses the segments to match segments in said medication instruction to segments in the lexicon and associate matched segments with corresponding identifier codes from the lexicon, the data processor analyzing segments not found in the lexicon and adding the segments to the lexicon after corresponding identifier codes having been assigned to the segments,
   wherein the data processor deconstructs the data into significant instructions and parses the significant instructions to reconstruct one or more medication instructions as one or more associated identifier codes, and wherein the data processor associates previously identified segments with corresponding identifier codes from the lexicon and generates identifier codes for segments not previously identified, wherein identifier codes for segments not previously identified are added to the lexicon for use in parsing significant instructions, wherein each identifier code is associated with an incrementing usage count to determine significant instruction priority for processing.

16. The system of claim 15, wherein the data processor associates a numerical identifier with each of the segments.

17. A computer-readable storage medium including a set of instructions for a computer, the set of instructions comprising:
   an extraction routine extracting at least one alphanumeric string containing significant instructions from a medication instruction, wherein said at least one alphanumeric string containing significant instructions comprises a free form alphanumeric string; and
   a parsing routine parsing the at least one alphanumeric string to associate at least one identifier with each of the at least one alphanumeric string,
   wherein the parsing routine:
      parses each of the one or more identified significant instructions to identify one or more words or phrases in each significant instruction;
      classifies known words or phrases in the one or more identified words or phrases according to a vocabulary by assigning an identifier from the vocabulary to each known word or phrase in the one or more identified words or phrases;
      analyzes unknown words or phrases in the one or more identified words and phrases to assign an identifier to each of the unknown words or phrases in the one or more identified words or phrases and adds the identifier for each of the unknown words or phrases to the vocabulary for use in significant instruction parsing, wherein the identifier is associated with an incrementing usage count to determine significant instruction priority for processing;
      reconstructs each of the one or more significant instructions as codified significant instructions using the identifiers associated with the known and unknown words or phrases in each of the identified significant instructions; and
      stores the one or more codified significant instructions in a medication order.

* * * * *

UNITED STATES PATENT AND TRADEMARK OFFICE
CERTIFICATE OF CORRECTION

PATENT NO. : 7,657,521 B2  Page 1 of 1
APPLICATION NO. : 11/107695
DATED : February 2, 2010
INVENTOR(S) : Masarie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this

Thirtieth Day of November, 2010

David J. Kappos
*Director of the United States Patent and Trademark Office*